United States Patent [19]
Rogers et al.

[11] Patent Number: 6,110,935
[45] Date of Patent: Aug. 29, 2000

[54] BENZOFURAZAN COMPOUNDS FOR ENHANCING GLUTAMATERGIC SYNAPTIC RESPONSES

[75] Inventors: Gary A. Rogers, Santa Barbara; Christopher M. Marrs, Foothill Ranch, both of Calif.

[73] Assignee: The Regents of the University of California, Oakland, Calif.

[21] Appl. No.: 08/800,108

[22] Filed: Feb. 13, 1997

[51] Int. Cl.[7] .................. A61K 31/445; A61K 31/43; C07D 211/00; C07D 241/00

[52] U.S. Cl. .................. 514/315; 514/320; 514/321; 514/315; 514/249; 514/319; 514/322; 514/328; 514/338; 514/258; 546/159; 546/193; 546/194; 546/199; 544/336; 544/349

[58] Field of Search ...................... 546/199, 159, 546/193, 194; 514/318, 322, 338, 328, 249, 258; 544/338, 349

[56] References Cited

U.S. PATENT DOCUMENTS

| | | | |
|---|---|---|---|
| 3,981,864 | 9/1976 | Tanaka et al. | 260/239 BG |
| 4,420,485 | 12/1983 | Davis et al. | 424/267 |
| 4,476,135 | 10/1984 | Neumann et al. | 424/270 |
| 5,032,604 | 7/1991 | Baldwin et al. | 514/361 |
| 5,112,824 | 5/1992 | Baldwin et al. | 514/253 |

FOREIGN PATENT DOCUMENTS

| | | |
|---|---|---|
| 0 431 943 A2 | 6/1991 | European Pat. Off. ...... C07D 491/10 |
| 0 709 384 | 5/1996 | European Pat. Off. |
| WO 94/02475 | 2/1994 | WIPO ............ C07D 317/68 |
| WO 97 36907 | 10/1997 | WIPO . |

OTHER PUBLICATIONS

Bauer et al., (J. Med. Chem. Chem. 1976, vol. 19, No. 11, pp. 1315–1324).

Parham et al., (J. Org. Chem., 1976, vol. 41, No. 15, pp. 2629–2633).

*Primary Examiner*—Jose' G. Dees
*Assistant Examiner*—Sabiha N. Qazi
*Attorney, Agent, or Firm*—Henry D. Coleman; R. Neil Sudol

[57] ABSTRACT

Compounds of the general structural formula

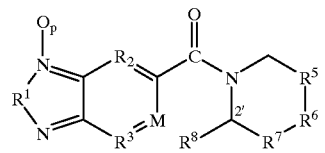

are shown to have AMPA receptor enhancing properties. The compounds are useful for such therapeutic purposes as facilitating the learning of behaviors dependent upon AMPA receptors, and in treating conditions, such as memory impairment, in which AMPA receptors, or synapses utilizing these receptors, are reduced in numbers or efficiency. They may also be used to enhance excitatory synaptic activity in order to restore an imbalance between brain subregions, as in treatment of schizophrenia or schizophreniform behavior.

8 Claims, 3 Drawing Sheets

BENZOFURAZAN COMPOUNDS FOR ENHANCING GLUTAMATERGIC SYNAPTIC RESPONSES

FIELD OF THE INVENTION

This invention relates to the prevention and treatment of cerebral insufficiency, including enhancement of receptor functioning in synapses in brain networks responsible for higher order behaviors. These brain networks are involved in cognitive abilities related to memory impairment, such as is observed in a variety of dementias, and in imbalances in neuronal activity between different brain regions, as is suggested in disorders such as schizophrenia. In a particular aspect, the invention relates to compounds useful for treatment of such conditions, and methods of using these compounds for such treatment.

BACKGROUND OF THE INVENTION

The release of glutamate at synapses at many sites in mammalian forebrain stimulates two classes of post-synaptic receptors. These classes are usually referred to as AMPA/quisqualate and N-methyl-D-aspartic acid (NMDA) receptors. AMPA/quisqualate receptors mediate a voltage independent fast excitatory post-synaptic current (the fast EPSC), whereas NMDA receptors generate a voltage-dependent, slow excitatory current. Studies carried out in slices of hippocampus or cortex indicate that the AMPA receptor mediated fast EPSC is generally the dominant component by far at most glutamatergic synapses.

AMPA receptors are not evenly distributed across the brain but rather are largely restricted to telencephalon and cerebellum. These receptors are found in high concentrations in the superficial layers of neocortex, in each of the major synaptic zones of hippocampus, and in the striatal complex, as reported by Monaghan et al., in Brain Research 324:160–164 (1984). Studies in animals and humans indicate that these structures organize complex perceptual-motor processes and provide the substrates for higher-order behaviors. Thus, AMPA receptors mediate transmission in those brain networks responsible for a host of cognitive activities.

For the reasons set forth above, drugs that enhance the functioning of AMPA receptors could have significant benefits for intellectual performance. Such drugs should also facilitate memory encoding. Experimental studies, such as those reported by Arai and Lynch, Brain Research 598:173–184 (1992), indicate that increasing the size of AMPA receptor-mediated synaptic response(s) enhances the induction of long-term potentiation (LTP). LTP is a stable increase in the strength of synaptic contacts that follows repetitive physiological activity of a type known to occur in the brain during learning.

Compounds that enhance the functioning of the AMPA form of glutamate receptors facilitate the induction of LTP and the acquisition of learned tasks as measured by a number of paradigms. See, for example, Granger et al., Synapse 15:326–329 (1993); Staubli et al., PNAS 91:777–781 (1994); Arai et al., Brain Res. 638:343–346 (1994); Staubli et al., PNAS 91:11158–11162 (1994); Shors et al., Neurosci. Let. 186:153–156 (1995); Larson et al., J. Neurosci. 15:8023–8030 (1995); Granger et al., Synapse 22:332–337 (1996); Arai et al., JPET 278:627–638 (1996); Lynch et al., Internat. Clin. Psychopharm. 11:13–19 (1996); and Lynch and Rogers, PCT Pubn. No. WO 94/02475. There is a considerable body of evidence showing that LTP is the substrate of memory. For example, compounds that block LTP interfere with memory formation in animals, and certain drugs that disrupt learning in humans antagonize the stabilization of LTP, as reported by del Cerro and Lynch, Neuroscience 49:1–6 (1992).

A possible prototype for a compound that selectively facilitates the AMPA receptor has been described by Ito et al., J. Physiol. 424:533–543 (1990). These authors found that the nootropic drug aniracetam (N-an-isoyl-2-pyrrolidinone) increases currents mediated by brain AMPA receptors expressed in Xenopus oocytes without affecting responses by γ-aminobutyric acid (GABA), kainic acid (KA), or NMDA receptors. Infusion of aniracetam into slices of hippocampus was also shown to substantially increase the size of fast synaptic potentials without altering resting membrane properties. It has since been confirmed that aniracetam enhances synaptic responses at several sites in hippocampus, and that it has no effect on NMDA-receptor mediated potentials. See, for example, Staubli et al., Psychobiology 18:377–381 (1990) and Xiao et al., Hippocampus 1:373–380 (1991).

Aniracetam has been found to have an extremely rapid onset and washout, and can be applied repeatedly with no apparent lasting effects, which are desirable features for behaviorally-relevant drugs. Aniracetam does present several disadvantages, however. The peripheral administration of aniracetam is not likely to influence brain receptors. The drug works only at high concentrations (approx. 1.0 mM), and about 80% of the drug is converted to anisoyl-GABA following peripheral administration in humans (Guenzi and Zanetti, J. Chromatogr. 530:397–406 (1990)). The metabolite, anisoyl-GABA, has been found to have less activity than aniracetam.

A class of AMPA receptor-enhancing compounds that does not display the low potency and inherent instability characteristic of aniracetam has been described (Lynch and Rogers, PCT Pubn. No. WO 94/02475). These compounds, termed "AMPAKINESI"™, are substituted benzamides which include, for example, 1-(1,3-benzodioxol-5-ylcarbonyl)piperidine. They are chemically more stable than aniracetam and show improved bioavailability as judged by experiments performed by Positron Emission Tomography (PET) (see, for example, Staubli et al., in PNAS 91:11158–11162 (1994).

Another class of Ampakines, benzoxazines, has been discovered recently to have very high activity in in vitro and in vivo models for assessing the probability of producing cognition enhancement, as described in copending application, "Benzoxazines for Enhancing Synaptic Response", by Rogers and Lynch. Some, but not all, of these compounds show activity in a rat model for the human disease, schizophrenia (Larson et al., Brain Res. 728: 353–356 (1996)).

Certain substituted benzofurazan and benzothiadiazole compounds have been found to be significantly and surprisingly more potent in the animal model of schizophrenia than previous compounds, and are also effective in cognition enhancement. These compounds are disclosed herein.

SUMMARY OF THE INVENTION

The present invention includes, in one aspect, a compound as shown by structure I, and described in Section II of the Detailed Description, following. Administration of compounds of this class has been found to increase synaptic responses mediated by AMPA receptors. The compounds are significantly and surprisingly more potent than previously described compounds in increasing AMPA receptor function in slices of rat hippocampus, in an animal model of schizophrenia, and in enhancing cognitive performance, such as performance in an 8-arm radial maze.

The ability of the compounds of the invention to increase AMPA receptor-mediated responses makes the compounds useful for a variety of purposes. These include facilitating the learning of behaviors dependent upon AMPA receptors, treating conditions in which AMPA receptors, or synapses utilizing these receptors, are reduced in numbers or efficiency, and enhancing excitatory synaptic activity in order to restore an imbalance between brain subregions.

In another aspect, the invention includes a method for the treatment of a mammalian subject suffering from a hypoglutamatergic condition, or from a deficiency in the number or strength of excitatory synapses, or in the number of AMPA receptors, such that memory or other cognitive functions are impaired. Such conditions may also cause a cortical/striatal imbalance, leading to schizophrenia or schizophreniform behavior. According to the method, such a subject is treated with an effective amount of a compound as shown by structure I, and described in Section II of the Detailed Description, following, in a pharmaceutically acceptable carrier.

These and other objects and features of the invention will become more fully apparent when the following detailed description of the invention is read in conjunction with the accompanying drawings.

DETAILED DESCRIPTION OF THE INVENTION

I. Definitions

Figure 1:
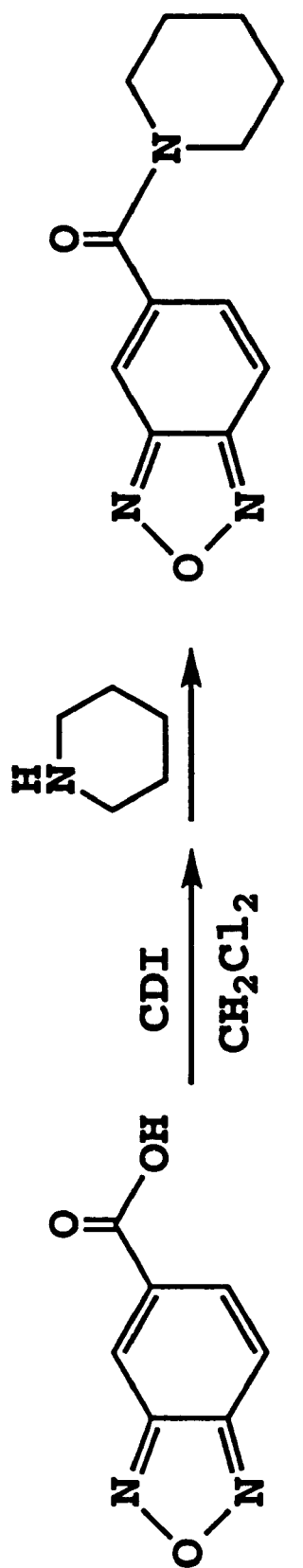
FIG. 1 shows a method of preparing a preferred compound of the invention.
Figure 3:
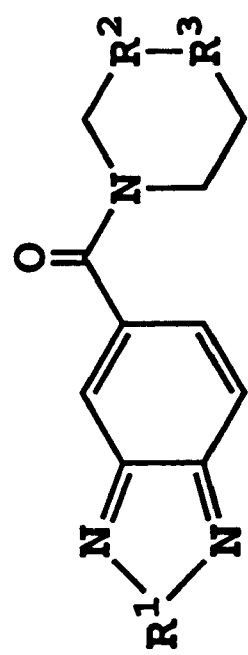
FIG. 3 represents a selection of compounds useful in practicing the method of the invention.

The terms below have the following meanings unless indicated otherwise.

"Alkyl" refers to a fully saturated monovalent radical containing carbon and hydrogen, and which may be cyclic, branched or a straight chain. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl, and cyclohexyl.

"Aryl" refers to a substituted or unsubstituted monovalent aromatic radical having a single ring (e.g., benzene) or multiple condensed rings (e.g., naphthyl). Other examples include heterocyclic aromatic ring systems having one or more nitrogen, oxygen, or sulfur atoms in the ring, such as imidazole, furyl, pyrrole, pyridyl, and indole.

The term "effective amount" refers to the amount of a selected compound of formula I which is necessary to enhance glutamatergic synaptic response by increasing AMPA receptor activity. The precise amount required will vary depending upon the particular compound selected, the age and weight of the subject, route of administration, and so forth, but may be easily determined by routine experimentation.

The term "pharmaceutically acceptable carrier" refers to a carrier or excipient which is not unacceptably toxic to the subject to which it is administered. Pharmaceutically acceptable excipients are described at length by E. W. Martin, in "Remington's Pharmaceutical Sciences."

II. AMPA Receptor Enhancing Compounds

The present invention is directed, in one aspect, to compounds having AMPA receptor enhancing properties.

These are compounds having the structure I, below:

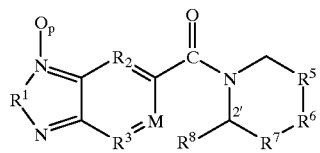

in which:

$R^1$ is oxygen or sulfur;

$R^2$ and $R^3$ are independently selected from the group consisting of —N=, —CR=, and —CX=;

M is =N— or =NR$^4$—, wherein $R^4$ and $R^8$ are independently R or together form a single linking moiety linking M to the ring vertex 2', the linking moiety being selected from the group consisting of a single bond, —CR$_2$—, —CR=CR—, —C(O)—, —O—, —S(O)$_y$—, —NR—, and —N=;

$R^5$ and $R^7$ are independently selected from the group consisting of —(CR$_2$)$_n$—, —C(O)—, —CR=CR—, —CR=CX—, —C(RX)—, —CX$_2$—, —S—, and —O—, and $R^6$ is selected from the group consisting of —(CR$_2$)$_m$—, —C(O)—, —CR=CR—, —C(RX)—, —CX$_2$—, —S—, and —O—;

wherein

X is —Br, —Cl, —F, —CN, —NO$_2$, —OR, —SR, —NR$_2$, —C(O)R, —CO$_2$R, or —CONR$_2$, and R is hydrogen, C$_1$–C$_6$ branched or unbranched alkyl, which may be unsubstituted or substituted with one or more functionalities defined above as X, or aryl, which may be unsubstituted or substituted with one or more functionalities defined above as X;

m and p are, independently, 0 or 1; and n and y are, independently, 0, 1 or 2.

Preferred subsets of the compounds encompassed by formula I include those in which p is 0, those in which $R^2$ and $R^3$ are —CR= and M is =NR$^4$, particularly where $R^4$ is hydrogen, and those in which $R^1$ is oxygen. A particularly preferred subset is one in which all of the above qualifications apply, and preferably in which $R^5$ and $R^7$ are —(CR$_2$)— and $R^6$ is —(CR$_2$)$_m$—; that is, certain 5-carboxamido benzofurazan derivatives containing different-sized saturated heterocyclic rings bonded to the carbonyl group. A particularly preferred compound of this group is 1-(benzofurazan-5-ylcarbonyl)piperidine, designated herein as compound 2. Also preferred is the corresponding compound in which $R^1$ is sulfur; that is, 1-(benzo-2,1,3-thiadiazole-5-ylcarbonyl)piperidine, designated herein as compound 1.

A second preferred subset of the compounds of formula I is that in which p is 0, $R^4$ and $R^8$ are both hydrogen, $R^5$ is —CR=CX— or —CR=CR—, $R^6$ is —(CR$_2$)$_m$—, and $R^7$ is —(CR$_2$)$_n$—. A further preferred class of this second subset is that in which m is 0. Particularly preferred examples of this class are those compounds in which $R^1$ is oxygen, n is 1, and R is hydrogen, that is, 1-(benzofurazan-5-ylcarbonyl)-1,2,3,6-tetrahydropyridine, designated herein as compound 3, and 1-(benzofurazan-5-ylcarbonyl)-1,2,3,6-tetrahydro-4-fluoropyridine, designated herein as compound 6.

A third preferred subset of formula I includes those compounds in which p is 0, $R^1$ is oxygen, $R^4$ and $R^8$ are both hydrogen, $R^5$ and $R^7$ are —$(CR_2)_n$—, and $R^6$ is —C(O)—, —C(RX)—, $CX_2$—, —O—, or —S—. A further preferred class of this third subset is that in which $R^6$ is —CRX— or —$CX_2$—, where R and X are each selected from the groups defined above. Two particularly preferred examples of this class are those in which X is fluorine, n is 1, and R is hydrogen; that is, 1-(benzofurazan-5-ylcarbonyl)-4'-fluoropiperidine and 1-(benzofurazan-5-ylcarbonyl)-4',4'-difluoropiperidine, designated herein as compounds 4 and 5, respectively.

Another preferred class of this third subset is that in which n is 1, R is hydrogen, and $R^6$ is oxygen or sulfur. This class includes morpholino and thiomorpholino amides of benzofurazan, i.e. N-(benzofurazan-5-ylcarbonyl)morpholine and N-(benzofurazan-5-ylcarbonyl)thiomorpholine.

A fourth preferred subset of the compounds of formula I is that in which M is =$NR^4$—, where $R^4$ and $R^8$ together form a single linking moiety linking M to the ring vertex 2'. This linking moiety is selected from the group consisting of a single bond, —$CR_2$—, —CR=CR—, —C(O)—, —O—, —S—, —NR—, and —N=. Preferred compounds of this fourth subset include those in which p is 0, those in which $R^1$ is oxygen, and those in which $R^2$ and $R^3$ are —CR=, where R is defined as above. Particularly preferred compounds are those in which all of the above qualifications apply; that is, certain tetracyclic benzofurazan amides, such as those represented in FIG. 2. A preferred group of these compounds includes those in which the linking moiety is selected from —$CR_2$—, —O—, —S—, and —N=. Preferably, $R^5$ and $R^7$ are —$(CR_2)_n$—, and $R^6$ is —$(CR_2)_m$—. More preferably, in this case, n is 1, and m is 0 or 1, giving a 5-membered or 6-membered heterocyclic ring, respectively, as the rightmost fused ring. Of the preferred linking moieties, —$CR_2$—, oxygen, sulfur, and —N=, oxygen and imino (—N=) are particularly preferred, with oxygen being most preferred.

III. Preparation of Subject Compounds

The compounds of the present invention can be synthesized in a variety of ways, using conventional synthetic chemistry techniques. Methods for the preparation of the compounds of the present invention include the following.

Compounds of the invention in which $R^4$ and $R^8$ do not form a linking moiety are conveniently prepared, as shown in FIG. 1, by activation of the carboxyl group of an appropriately substituted benzoic acid, or, alternatively, a nicotinic, pyrazinoic, pyridizine carboxylic, or pyrimidine carboxylic acid, with carbonyldiimidazole or another activating group, such as, but not limited to, thionyl chloride, in an anhydrous solvent such as dichloromethane, chloroform, tetrahydrofuran, ethyl acetate, or the like, followed by addition of a suitable cyclic amine.

Compounds of the invention in which $R^4$ and $R^8$ form a linking moiety may be prepared according to methods such as those shown in FIGS. 2A–2D. Although the illustrated preparations employ a benzofurazan nucleus, similar methods may be used to prepare other compounds of the invention, e.g. the corresponding benzothiadiazoles and other nitrogen-containing heteroaromatic systems.

Figure 2A:
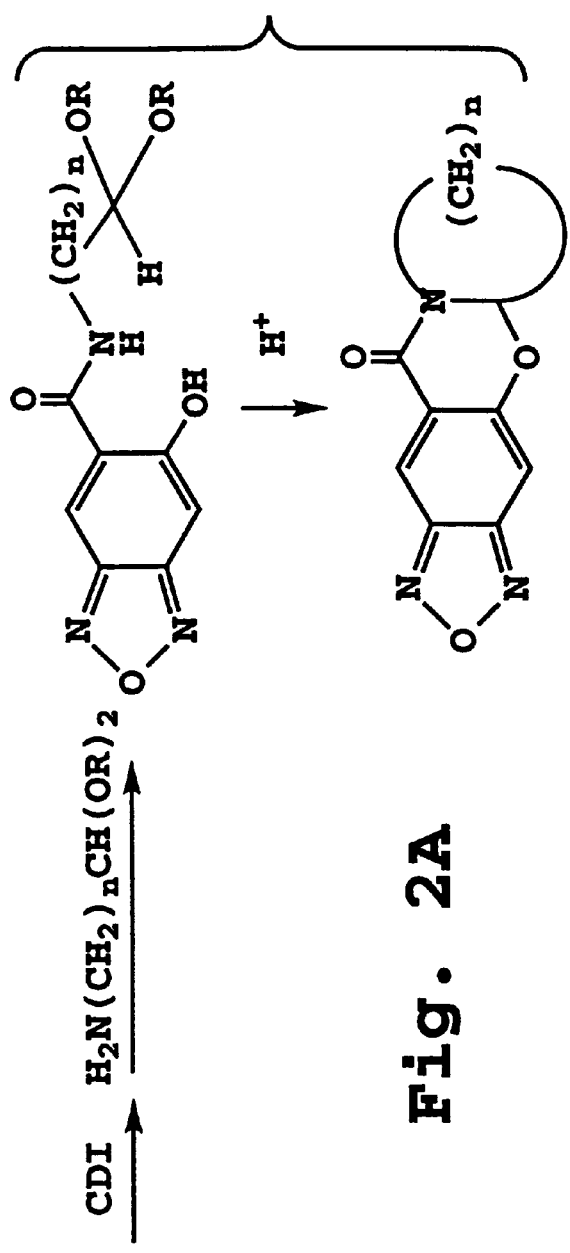
FIGS. 2A–2D show methods of preparing tetracyclic compounds that form one embodiment of the invention.
Figure 2B:
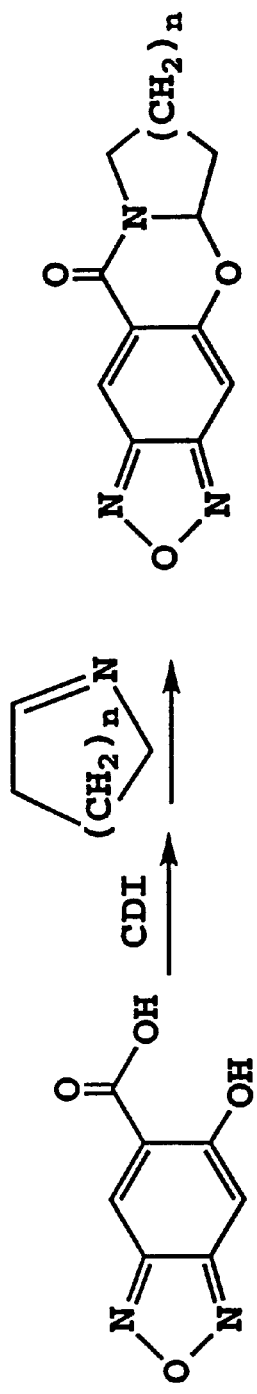

As shown in FIG. 2A, activation of the carboxyl group of an appropriately substituted salicylic acid with carbonyldiimidazole, in an anhydrous solvent such as dichloromethane, chloroform, tetrahydrofuran, ethyl acetate, or the like, is followed by addition of a suitable aminoalkylacetal. The resulting amide acetal is treated with a strong acid, such as an alkyl or aryl sulfonic acid, or trifluoroacetic acid in a solvent of low basicity, such as dichloromethane, to effect cleavage of the acetal and cyclization to a tetracyclic substituted benzoxazine, as shown, in which the linking moiety formed by $R^4$ and $R^8$ is oxygen. An alternative method of preparation, shown in FIG. 2B, reacts the activated salicylate with a cyclic imine, such as 1-pyrroline or 2,3,4,5-tetrahydropyridine.

Figure 2C:
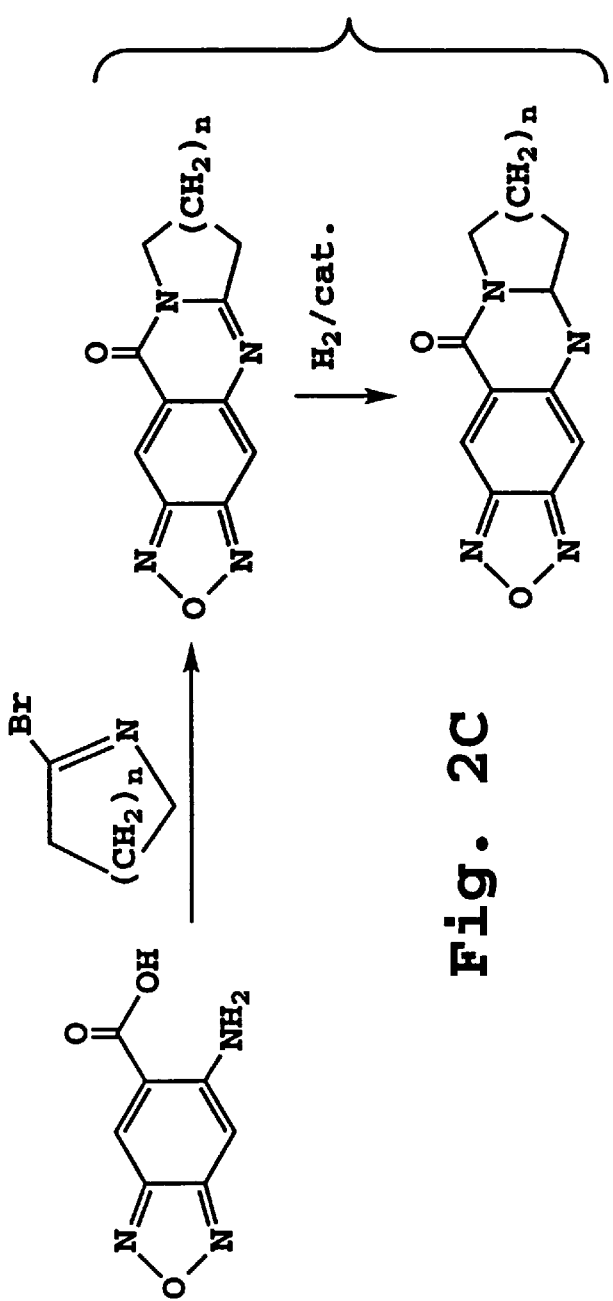

FIG. 2C shows the reaction of a suitably substituted anthranilate ester with a cyclic haloimine, such as a 2-chloro- or 2-bromoimidate, to yield a tetracyclic compound in which the linking moiety formed by $R^4$ and $R^8$ is an imino group. This group may be subsequently reduced by, for example, catalytic hydrogenation, to give an amino linking moiety.

Figure 2D:
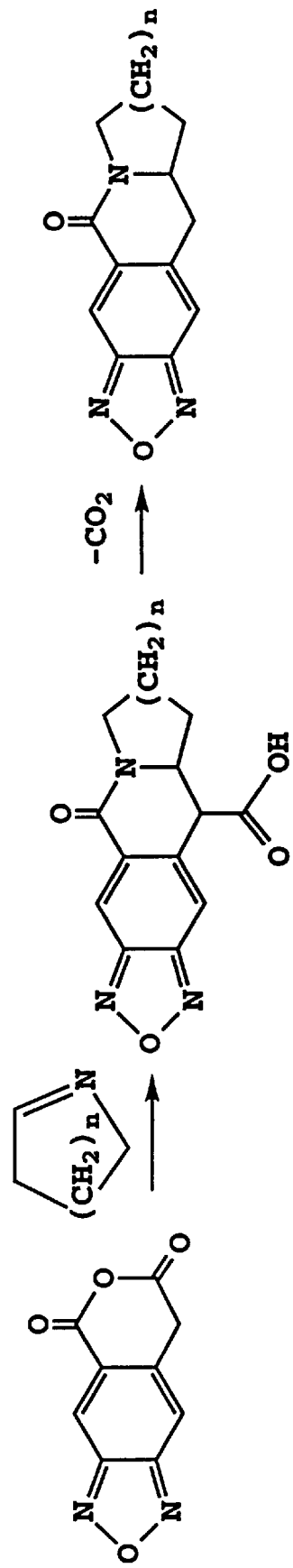

FIG. 2D shows the reaction of a suitably substituted homophthalic anhydride with a cyclic imine, such as 1-pyrroline or 2,3,4,5-tetrahydropyridine, followed by decarboxylation, to yield a tetracyclic compound in which the linking moiety formed by $R^4$ and $R^8$ is a —$CH_2$—, or —$CR_2$— group. (See, for example, Cushman et al., *J. Org. Chem.* 45:5067–5073 (1980), and Smith et al., *J. Heterocyclic Chem.* 28:1813–1815 (1991).)

Examples 1–5 describe preparation of representative compounds of the invention according to the methods described above.

IV. Method of Treatment

According to one aspect of the invention, a method is provided for treating a mammalian subject which suffers from a hypoglutamatergic condition, or from deficiencies in the number or strength of excitatory synapses or in the number of AMPA receptors. In such a subject, memory or other cognitive functions may be impaired, or cortical/striatal imbalance may occur, leading to schizophrenia or schizophreniform behavior. The method of treatment comprises administering to the subject, in a pharmaceutically acceptable carrier, an effective amount of a compound having the formula:

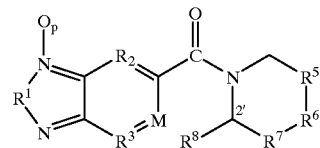

wherein $R^1$ is oxygen or sulfur;

$R^2$ and $R^3$ are independently selected from the group consisting of —N=, —CR=, and —CX=;

M is =N— or =$NR^4$—, wherein $R^4$ and $R^8$ are independently R or together form a single linking moiety linking M to the ring vertex 2', the linking moiety being selected from the group consisting of a single bond, —$CR_2$—, —CR=CR—, —C(O)—, —O—, —$S(O)_y$—, —NR—, and —N=;

$R^5$ and $R^7$ are independently selected from the group consisting of —$(CR_2)_n$—, —C(O)—, —CR=CR—, —CR=CX—, —C(RX)—, —$CX_2$—, —S—, and —O—, and $R^6$ is selected from the group consisting of —$(CR_2)_m$—, —C(O)—, —CR=CR—, —C(RX)—, —$CX_2$—, —S—, and —O—;

wherein

X is —Br, —Cl, —F, —CN, —$NO_2$, —OR, —SR, —$NR_2$, —C(O)R, —$CO_2$R, or —$CONR_2$, and R is hydrogen, $C_1$–$C_6$ branched or unbranched alkyl, which may be unsubstituted or substituted with one or more functionalities defined above as X, or aryl, which may be unsubstituted or substituted with one or more functionalities defined above as X;

m and p are, independently, 0 or 1; and n and y are, independently, 0, 1 or 2.

Of the compounds administered according to the method, preferred groups include those described in Section II, above. Particularly preferred are those compounds designated as compounds 1 through 6, with compound 2 being most preferred.

As noted above, treatment of a subject according to the method of the invention is useful for enhancing AMPA receptor activity, and thus may be used to facilitate the learning of behaviors dependent upon AMPA receptors, and to treat conditions, such as memory impairment, in which AMPA receptors, or synapses utilizing these receptors, are reduced in numbers or efficiency. The method is also useful for enhancing excitatory synaptic activity in order to restore an imbalance between brain subregions, which may manifest itself in schizophrenia or schizophreniform behavior. The compounds administered in accordance with the method have been found to be more effective than previously described compounds in enhancing AMPA receptor activity, as shown in the in vitro and in vivo tests described below.

V. Biological Activity

A. Enhancement of AMPA Receptor Function

Synaptic responses mediated by AMPA receptors are increased according to the method of the invention, using the compounds described herein. These compounds are demonstrated, in the Examples that follow, to be substantially more potent than previously-described compounds in increasing AMPA receptor function in slices of rat hippocampus. This in vitro assay is described as follows, and in Example 6, below.

The field EPSP (excitory post-synaptic potential) recorded in field CA1 after stimulation of CA3 axons is known to be mediated by AMPA receptors, which are present in the synapses (Kessler et al., Brain Res. 560: 337–341 (1991)). Drugs that selectively block the receptor selectively block the field EPSP (Muller et al., Science, supra). Aniracetam, which has been shown to increase the mean open time of the AMPA receptor channel, increases the amplitude of the synaptic current and prolongs its duration (Tang et al., Science, supra). These effects are mirrored in the field EPSP (see, for example, Staubli et al., Psychobiology, supra; Xiao et al., Hippocampus, supra; Staubli et al., Hippocampus 2: 4958 (1992)). Similar results have been reported for the previously disclosed stable benzamide analogs of aniracetam (Lynch and Rogers, PCT Pubn. No. WO 94/02475).

To obtain the data shown in Table I, a bipolar nichrome stimulating electrode was positioned in the dendritic layer (stratum radiatum) of the hippocampal subfield CA1 close to the border of subfield CA3, as described in Example 6. Current pulses (0.1 msec) through the stimulating electrode activate a population of the Schaffer-commissural (SC) fibers, which arise from neurons in the subdivision CA3 and terminate in synapses on the dendrites of CA1 neurons. Activation of these synapses causes them to release the transmitter glutamate. Glutamate binds to the post-synaptic AMPA receptors which then transiently open an associated ion channel and permit a sodium current to enter the postsynaptic cell. This current results in a voltage in the extracellular space (the field EPSP), which is recorded by a high impedance recording electrode positioned in the middle of the stratum radiatum of CA1.

The intensity of the stimulation current was adjusted to produce half-maximal EPSPs (typically about 1.5–2.0 mV). Paired stimulation pulses were given every 40 sec with an interpulse interval of 200 msec, as described further in Example 6.

Hippocampal slices were maintained in a recording chamber continuously perfused with artificial cerebrospinal fluid (ACSF). During 15–30 minute intervals, the perfusion medium was switched to one containing various concentrations of the test compounds. Responses collected immediately before and at the end of drug perfusion were superimposed in order to calculate the percent increase in EPSP amplitude.

Invention compounds 1–6, as shown in FIG. 1, and reference compound CX516, disclosed in PCT Pubn. No. WO 94/02475, were assayed in the physiological test system described above. The first data column of Table 1, below, shows the estimate of the concentration of each test compound that would be required to increase the amplitude of the field EPSP to a value 10% above the baseline level.

TABLE 1

| Compound # | $R^1$ | $R^5$ | $R^6$ | Amp[1] ($\mu M$) | $MED_S$[2] (mg/kg) | $MED_C$[3] (mg/kg) |
|---|---|---|---|---|---|---|
| CX516 | $C_2H_2$ | $CH_2$ | $CH_2$ | 80 | 10 | 15 |
| 1 | S | $CH_2$ | $CH_2$ | 30 | ND | ND |
| 2 | 0 | $CH_2$ | $CH_2$ | 3 | 0.1 | 2 |
| 3 | 0 | CH | CH | 100 | ND | ND |
| 4 | 0 | $CH_2$ | CHF | 30 | 1 | ND |
| 5 | 0 | $CH_2$ | $CF_2$ | 50 | 1 | ND |
| 6 | 0 | CH | CF | 30 | ND | ND |

[1]Concentration of compound that causes a 10% increase in the amplitude of the field EPSP in field CA1 of rat hip-pocampal slice.
[2]Minimum Effective Dose that produces a statistically significant improvement in behavior in the animal model of schizophrenia.
[3]Minimum Effective Dose that produces a statistically significant improvement in behavior in the eight-arm radial maze task for cognition/memory enhancement.
ND = Not determined As the data in Table 1 show, the present compounds produced a dose-dependent increase in the amplitude of the EPSP and were effective at concentrations as low as 3 uM. The majority of the tested compounds were equally or more effective than the reference compound, CX516(1-(quinoralin-6-ylcarbonyl) piperidine), in increasing AMPA receptor function. Compounds 1, 2, 4, 5 and 6 showed superior results, and compound 2 was approximately 27 times as effective as the reference compound.

Studies that compared the effects of AMPA modulators on monosynaptic (as reported here) and polysynaptic responses demonstrated that a 10% increase in the amplitude of the monosynaptic field EPSP was amplified to an increase of 300% on a trisynaptic response (Servio et al., Neuroscience 74: 1025–1035 (1996)). Furthermore, the concentration of the modulator that evoked these responses was shown to exist in plasma from behaviorally relevant doses (Granger et al., Synapse, supra). Thus, a 10. increase in amplitude of the monosynaptic field EPSP, as reported in the table, is likely to represent a behaviorally relevant plasma concentration.

B. Behavioral Testing

The compounds of the invention are also effective in relevant animal models of disease, such as schizophrenia, and in models of cognitive performance, such as performance in an 8-arm radial maze.

The second data column in Table 1 shows the Minimum Effective Dose ($MED_S$) for efficacy in the methamphetamine/rat model, which has proven useful in assessing the probable efficacy of neuroleptic drugs for the treatment of schizophrenia (Larson et al., Brain Res., supra). The dose recorded is that which reduced the hyperactivity and/or the stereotypic activity induced by acute administration of 2 mg/kg methamphetamine in rats, as described in Example 7.

All of the compounds tested were significantly more effective than the reference compound, as shown in the Table, in that a ten-fold or greater reduction in dose produced an equivalent effect. Compound 2 was equally effective at a hundred-fold reduction in dose.

The third data column shows the MED for efficacy to improve performance in the eight-arm radial maze task, which tests for improved memory and cognition ($MED_c$). This task has been described previously (Staubli et al., *PNAS* 91:777–781 (1994)) and Lynch and Rogers, PCT Pubn. No. WO 94/02475). Compound 2 was several times more potent than CX516 in this test.

VI. Administration, Dosages, and Formulation

As noted above, the compounds and method of the invention increase AMPA receptor-mediated responses, and are useful for the treatment of hypoglutamatergic conditions. They are also useful for treatment of con- ditions such as impairment of memory or other cognitive functions, brought on by a deficiency in the number or strength of excitatory synapses, or in the number of AMPA receptors. They may also be used in the treatment of schizophrenia or schizophreniform behavior resulting from a cortical/striatal imbalance, and in facilitation of learning of behaviors dependent upon AMPA receptors.

Generally, dosages and routes of administration of the compound will be determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, or intramuscular injection. Subjects contemplated for treatment according to the method of the invention include humans, domesticated animals, laboratory animals, and the like.

Formulations containing the compounds of the invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20%), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or will be apparent to those skilled in the art; for example, see "Remington's Pharmaceutical Sciences" (17th Ed., Mack Pub. Co, 1985). The composition to be administered will contain a quantity of the selected compound in a pharmaceutically effective amount for effecting increased AMPA receptor currents in a subject.

The following examples illustrate but are not intended in any way to limit the invention. Unless otherwise stated, all temperatures are given in degrees Celsius. All $^1$H NMR spectra were obtained in deuterochloroform as solvent using tetramethylsilane as an internal standard. Infrared (IR) spectra were recorded as thin films on a Fresnel crystal in a ATI Mattson Gemini series FTIR.

EXAMPLE 1

1-(Benzo-2,1,3-thiadiazole-5-ylcarbonyl)piperidine (1)

Trimethylaluminum (2M in toluene; 3.0 mL, 6.0 mmol) was diluted into 30 mL dichloromethane to which piperidine (0.55 g, 6.5 mmol) and methyl benzo-2,1,3-thiadiazole-5-carboxylate (1.16 g, 6.00 mmol) were added. The reaction was stirred at room temperature for 2 hours and concentrated to one-half the volume by rotary evaporation. Dry toluene (25 mL) was added and the reaction solution was heated to 80° C. for 1 hour. Additional piperidine (about 0.2 g) was added and the temperature was increased to 100° C. for 1 hour. The solution was allowed to cool to room temperature and stirred overnight, at which time it was quenched with 10% citric acid and hydrochloric acid. The solution was diluted with ethyl acetate and sequentially washed with 10% citric acid, saturated sodium hydrogen phosphate and saturated sodium chloride, and subsequently dried over anhydrous sodium sulfate. The solution was concentrated onto silica and product was eluted with hexane/ethyl acetate (3:1). Purification by distillation in a kugelrohr at 180° C. and 0.5 mmHg yielded 1-(benzo-2,1,3-thiadiazole-5-ylcarbonyl)piperidine, 1 (1.29 g, 87%) as a pale yellow oil. IR: 2920, 2855, 1633, 1478, 1439, 1280, 1223, 1001, 816, and 748 cm$^{-1}$. $^1$H NMR (500 MHz): δ 8.06 (1H, d, J=9.1 Hz); 8.02 (1H, s); 7.63 (1H, t, J=9.0 and 1.5 Hz); 3.77 (2H, br s); 3.40 (2H, br s); 1.72 (4H, br s); and 1.57 ppm (2H, br s).

EXAMPLE 2

1-(Benzofurazan-5-ylcarbonyl)piperidine (2)

Benzofurazan-5-carboxylic acid (2.0 g, 12.2 mmol) was suspended in 10 mL dichloromethane. Carbonyl diimidazole (2.0 g, 12.3 mmol) was added, which caused dissolution with gas evolution. The resulting yellow solution was stirred for 40 minutes at room temperature, following which, piperidine (1.2 g, 14.1 mmol) was added. The solution was stirred overnight and then concentrated onto silica. Product was eluted with hexane/ethyl acetate (2:1) and purified by distillation in a kugelrohr at 155–170° C. and 0.5 mmHg. 1-(Benzofurazan-5-ylcarbonyl)piperidine, 2 (2.78 g, 99%), initially a pale yellow oil, crystallized upon cooling. M.p. 88.5–90.5° C. IR: 2938, 2857, 1630, 1519, 1439, 1266, 1223, 996, 881, 816, and 740 cm$^{-1}$. $^1$H NMR (500 MHz): δ 7.90 (1H, d, J=9.7 Hz); 7.84 (1H, s); 7.44 (1H, dd, J=9.4 and 1.4 Hz); 3.74 (2H, br s); 3.39 (2H, br s); 1.72 (4H, br s); and 1.57 ppm (2H, br s).

EXAMPLE 3

1-(Benzofuroxan-5-ylcarbonyl)piperidine

Benzofuroxan-5-carboxylic acid (1 g, 5.6 mmol) was suspended with stirring in 15 mL dichloromethane to which was added carbonyl diimidazole (0.90 g, 5.6 mmol). Gas evolved and the resulting solution was stirred for 40 minutes at which time piperidine (0.5 g, 5.9 mmol) was added with stirring. The reaction solution was concentrated onto silica and product was eluted with hexane/ethyl acetate (3:1). Recrystallization from 2-propanol/hexane (1:10) yielded 1-(benzofuroxan-5-ylcarbonyl)piperidine (0.94 g, 69%) as a yellow solid with m.p. 94.5–96.5° C. IR: 2938, 2855, 1620, 1612, 1528, 1487, 1435, 1257, 1233, 1018, 1000, 852, 811, and 747 cm$^{-1}$. $^1$H NMR (500 MHz): δ 7.10–7.80 (3H, br s); 3.72 (2H br s); 3.39 (2H, br s); 1.72 (4H, br s); and 1.54 ppm (2H, br s).

EXAMPLE 4

1-(Benzofurazan-5-ylcarbonyl)-1.2,3,6-tetrahydropyridine (3) and 1-(Benzofurazan-5-ylcarbonyl)-4-fluoropiperidine (4)

N-Trifluoroacetyl-4-hydroxypiperidine (7.92 g, 40 mmol) was suspended in 10 mL dicloromethane and cooled to −78° C. Diethylaminosulfurtrifluoride (6.8 g, 42 mmol) was added and the suspension was allowed to warm to room temperature overnight. The reaction mixture was then diluted with 125 mL dicloromethane and washed with saturated sodium bicarbonate solution, which resulted in vigorous bubbling. The dicloromethane solution was then dried by washing with a saturated sodium chloride solution followed by treatment with anhydrous magnesium sulfate. The solvent was removed in vacuo and the resulting orange oil was stirred with a 7.5 M KOH solution for 1h at room temperature. The product was extracted into ether and dried with anhydrous magnesium sulfate. The solution was filtered and the ether was removed by atmospheric distillation. The amines were distilled at 950° C. to yield 0.7 g colorless oil, which consisted of a mixture of 4-fluoropiperidine/1,2,3,6-tetrahydropyridine. IR: 3317, 3293, 2968, 2955, 2943, 2929, 1451, 1427, 1418, 1377, 1279, and 1023 cm$^{-1}$.

Benzofurazan-5-carboxylic acid (0.75 g, 4.6 mmol) was suspended in 15 mL dichloromethane. Carbonyl diimidazole (0.75 g, 4.6 mmol) was added to this suspension, which caused the reaction mixture to turned yellow as gas evolved. The solution was stirred for 30 minutes, at which time a mixture of 4-fluoropiperidine and 1,2,3,6-tetrahydropyridine (0.7 g, approximately 7 mmol) was added. The solution was stirred for 2 hours at room temperature, at which time the reaction mixture was concentrated onto silica and products were eluted with hexane/ethyl acetate (3:1). Three components were isolated in 100 mg, 200 mg and 300 mg yields. The second eluted compound solidified upon standing and was identified as 1-(benzofurazan-5-ylcarbonyl)-1,2,3,6-tetrahydropyridine, 3 by NMR. M.p. 68.5–70° C. IR: 1630, 1516, 1438, 1245, 1009, 881, 816, 741, and 629 cm$^{-1}$. $^1$H NMR (500 MHz): δ 7.92 (1H, d, J=9.0 Hz), 7.88 (1H, s), 7.47 (1H, d, J=9.0 Hz); 5.57–5.95 (2H, m); 4.23 (1H, br s); 3.90–3.97 (2H, m); 3.53 (1H, br s); 2.33 (1H, br s); and 2.22 ppm (1H, br s).

The third eluted component was recrystallized from ethyl acetate/hexane (1:10) to yield 200 mg white crystals with m.p. 124–125.50° C. and was identified as 1-(benzofuroxan-5-ylcarbonyl)-4'-fluoropiperidine, 4 by NMR. IR: 1633, 1439, 1274, 1231, 1034, 923, 881, and 742 cm$^{-1}$. $^1$H NMR (500 MHz): δ 7.93 (1H, d, J=9.0 Hz); 7.87 (1H, s); 7.44 (1H, d, J=9.0 Hz); 4.9–5.1 (1H, m); 4.0–4.2 (1H, br s); 3.5–3.7 (2H, m); 3.4–3.5 (1H, br s); and 1.7–2.1 ppm (4H, m).

A more direct route of synthesis of 1-(benzofurazan-5-ylcarbonyl)-1,2,3,6-tetrahydropyridine (3) was also performed in a manner similar to Example 2 above starting with pure tetrahydropyridine. Crude product (94% yield) was purified by silica gel chromatography (hexane/ethyl acetate; 1:3), which produced a 74% yield of pale yellow crystals with m.p. 82–83.5° C.; presumably a different crystal isomorph from that obtained above.

EXAMPLE 5

1-(Benzofurazan-5-ylcarbonyl)-4,4-difluoropiperidine (5) and 1-(Benzofurazan-5-ylcarbonyl)-1,2,3,6-tetrahvdro-4-fluorolyridine (6)

N-Trifluoroacetyl-4-piperidone (10 g, 52 mmol) was suspended in 10 mL dicloromethane. To this suspension, diethylaminosulfurtrifluoride (9.1 g, 56.5 mmol) was added. The reaction proceeded slowly at first but brought the mixture to a rolling boil within a few minutes. Cooling was applied to moderate the reaction. The mixture was stirred overnight, diluted with 125 mL dicloromethane and washed with saturated sodium bicarbonate solution, upon which vigorous bubbling was observed. The dicloromethane was then dried with a saturated sodium chloride solution followed by anhydrous magnesium sulfate. The solvent was removed in vacuo and the resulting orange oil was stirred with a 7.5 M KOH solution for 1h at room temperature. The product was extracted into ether, and the solution was dried with anhydrous magnesium sulfate and filtered. The ether was removed by atmospheric distillation, and the product was distilled at 105–125° C. to yield 4.5 g pale yellow oil, consisting of a mixture of 4,4-difluoropiperidine/1,2,3,6-tetrahydro-4-fluoropiperidine. IR: 2960, 1357, 1265, 1146, 1117, 987, 952, 814, and 792 cm$^{-1}$.

Benzofurazan-5-carboxylic acid (0.75 g, 4.6 mmol) was activated in 15 mL dichloromethane with carbonyl diimidazole as above in Example 4. A mixture of 4,4-difluoropiperidine and 1,2,3,6-tetrahydro-4-fluoropyridine (0.7 g) was added to the solution, which was stirred for 2 hours. The reaction mixture was concentrated onto silica and product was eluted with hexane/ethyl acetate (3:1) yielding two components. The first eluted component was recrystallized from ethyl acetate/hexane (1:5) yielding 480 mg of solid with m.p. 148–149° C. and was identified as 1-(benzofurazan-5-ylcarbonyl)-4,4'-difluoropiperidine, 5. IR: 1642, 1440, 1365, 1266, 1123, 1086, 936, 822, 817, 737, 607 cm$^{-1}$. $^1$H NMR (500 MHz): δ 7.96 (1H, d, J=9.5 Hz); 7.90 (1H, s); 7.45 (1H, t, J=8.8 and 1.1 Hz); 3.8–4.1 (2H, br s); 3.5–3.7 (2H, br s); and 1.9–2.2 ppm (4H, br d).

The second eluted component was recrystallized from ethyl acetate/hexane (1:10) yielding 180 mg solid with m.p. 102–105° C. and was identified as 1-(benzofurazan-5-ylcarbonyl)-1,2,3,6-tetrahydro-4-fluoropyridine, 6. IR: 1639, 1436, 1361, 1241, 1146, 1007, 828, 817, 742, 605 cm$^{-1}$. $^1$H NMR (500 MHz): δ 7.94 (1H, d, J=9.0 Hz); 7.90 (1H, s); 7.46 (1H, d, J=9.0 Hz); 5.1–5.4 (1H, m); 4.3 (1H, br s); 4.0 (2H, br s); 3.65 (1H, br s); and 2.30–2.55 ppm (2H, br d).

EXAMPLE 6

In Vitro Physiological Testing

The physiological effects of invention compounds were tested in vitro with slices of rat hippocampus according to the following procedure. Excitatory responses (field EPSPs) were measured in hippocampal slices, which were maintained in a recording chamber continuously perfused with artificial cerebrospinal fluid (ACSF). During a 15–30 minute interval, the perfusion medium was switched to one containing various concentrations of the test compounds. Responses collected immediately before and at the end of drug perfusion were superimposed in order to calculate the percent increase in EPSP amplitude.

To conduct these tests, the hippocampus was removed from anesthetized, 2 month old Sprague-Dawley rats and in vitro slices (400 micrometers thick) were prepared and maintained in an interface chamber at 35° C. using conventional techniques [see, for example, Dunwiddie and Lynch, J. Physiol. 276: 353–367 (1978)]. The chamber was constantly perfused at 0.5 mL/min with ACSF containing (in mM): NaCl 124, KCl 3, KH$_2$PO$_4$ 1.25, MgSO$_4$ 2.5, CaCl$_2$ 3.4, NaHCO$_3$ 26, glucose 10 and L-as-corbate 2. A bipolar nichrome stimulating electrode was positioned in the dendritic layer (stratum radiatum) of the hippocampal subfield CA1 close to the border of subfield CA3.

Current pulses (0.1 msec) through the stimulating electrode activate a population of the Schaffer-commissural (SC) fibers which arise from neurons in the subdivision CA3 and terminate in synapses on the dendrites of CA1 neurons. Activation of these synapses causes them to release the transmitter glutamate. Glutamate binds to the post-synaptic AMPA receptors which then transiently open an associated ion channel and permit a sodium current to enter the postsynaptic cell. This current results in a voltage in the extracellular space (the field EPSP) which is recorded by a high impedance recording electrode positioned in the middle of the stratum radiatum of CA1.

For the experiments summarized the table, the intensity of the stimulation current was adjusted to produce half-maximal EPSPs (typically about 1.5–2.0 mV). Paired stimulation pulses were given every 40 sec with an interpulse interval of 200 msec (see below). The field EPSPs of the second response were digitized and analyzed to determine amplitude. If the responses were stable for 15–30 minutes (baseline), test compounds were added to the perfusion lines for a period of about 15 minutes. The perfusion was then changed back to regular ACSF.

Paired-pulse stimulation was used since stimulation of the SC fibers, in part, activates interneurons which generate an inhibitory postgynaptic potential (IPSP) in the pyramidal cells of CA1. This feed forward IPSP typically sets in after the EPSP reaches its peak. It accelerates the repolarization and shortens the decay phase of the EPSP, and thus could partially mask the effects of the test compounds. One of the relevant features of the feed-forward IPSP is that it can not be reactivated for several hundred milliseconds following a stimulation pulse. This phenomenon can be employed to advantage to eliminate IPSP by delivering paired pulses separated by 200 milliseconds and using the second ("primed") response for data analysis.

The first data column of Table I shows the estimate of the concentration of each test compound that would be required to increase the amplitude of the field EPSP to a value 10% above the baseline level. Values were estimated by interpolation in most cases, but by extrapolation from determined values for others.

EXAMPLE 7

Behavioral Testing

The second data column in Table 1 shows the Minimum Effective Dose (MEDS) for activity in a methamphetamine/rat model for assessing the probable efficacy of neuroleptic drugs for the treatment of schizophrenia (Larson et al., Brain Res., supra). The dose recorded is that which reduced the hyperactivity and/or the stereotypic activity induced by acute administration of 2 mg/kg methamphetamine in Sprague-Dawley rats aged 2–4 months. Activity was monitored for 90 minutes using two rows of multiple, paired infrared diode-detectors such that the lower row detected locomotion and the upper row detected rearing behavior. Data were collected by and stored in a personal computer for later analysis.

The third data column in Table 1 shows the MED for efficacy to improve performance in the eight-arm radial maze task, which tests for improved memory and cognition (MED$_c$). This test has been described previously by Staubli et al., PNAS 91:777–781 (1994) and Lynch and Rogers, PCT Pubn. No. WO 94/02475.

While the invention has been described with reference to specific methods and embodiments, it will be appreciated that various modifications may be made without departing from the invention.

It is claimed:

1. A compound having the structure:

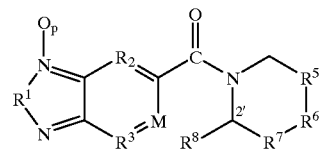

wherein:
  $R^1$ is oxygen or sulfur;
  $R^2$ and $R^3$ are independently selected from the group consisting of —N=, —CR=, and —CX=;
  M is =CR$^4$—;
  $R^4$ and $R^8$ are independently R;
  $R^5$ and $R^7$ are independently selected from the group consisting of —(CR$_2$)$_n$— and —C(RX)—;
  $R^6$ is selected from the group consisting of —(CR$_2$)$_m$— and —C(RX)—,
  wherein X is —Br, —Cl, —F, —CN, —NO$_2$, —OR, —SR, —C(O)R, —CO$_2$R, or —CONR$_2$;
  R is hydrogen;
  m and p are, independently, 0 or 1; and
  n is 0, 1 or 2.

2. A compound in accordance with claim 1 in which p is 0.

3. A compound in accordance with claim 1 in which $R^1$ is oxygen.

4. A compound in accordance with claim 1 in which $R^2$ and $R^3$ are —CR=.

5. A compound in accordance with claim 4 in which p is 0.

6. A compound in accordance with claim 2 in which $R^5$ and $R^7$ are —(CR$_2$)$_n$— and $R^6$ is —(CR$_2$)$_m$—.

7. A compound in accordance with claim 6 in which $R^1$ is oxygen, and m=n=1, said compound being 1-(benzofurazan-5-ylcarbonyl) piperidine.

8. A compound in accordance with claim 6 in which $R^1$ is sulfur, and m=n=1, said compound being 1-(benzo-2,1,3-thiadiazole-5-ylcarbonyl)piperidine.

* * * * *